United States Patent
Gagnon et al.

(10) Patent No.: US 9,101,273 B2
(45) Date of Patent: Aug. 11, 2015

(54) APPARATUS, DETECTOR, AND METHOD FOR APPLYING A PIXEL BY PIXEL BIAS ON DEMAND IN ENERGY DISCRIMINATING COMPUTED TOMOGRAPHY (CT) IMAGING

(75) Inventors: Daniel Gagnon, Twinsburg, OH (US); Xiaolan Wang, Buffalo Grove, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 428 days.

(21) Appl. No.: 13/531,141

(22) Filed: Jun. 22, 2012

(65) Prior Publication Data

US 2013/0343517 A1   Dec. 26, 2013

(51) Int. Cl.
| | |
|---|---|
| *H05G 1/56* | (2006.01) |
| *G01T 1/24* | (2006.01) |
| *A61B 6/03* | (2006.01) |
| *A61B 6/00* | (2006.01) |
| *G01T 1/29* | (2006.01) |
| *G01N 23/04* | (2006.01) |

(52) U.S. Cl.
CPC ............... *A61B 6/032* (2013.01); *A61B 6/4233* (2013.01); *A61B 6/4241* (2013.01); *A61B 6/54* (2013.01); *A61B 6/545* (2013.01); *G01N 23/04* (2013.01); *G01T 1/24* (2013.01); *G01T 1/2985* (2013.01); *G01N 2223/423* (2013.01); *G01N 2223/507* (2013.01); *H05G 1/56* (2013.01)

(58) Field of Classification Search
CPC ...... A61B 6/42; A61B 6/4208; A61B 6/4233; A61B 6/4266; A61B 6/545; H05G 1/56; G01T 1/175; G01T 1/24

USPC ........ 378/19, 62, 91, 95, 98.8, 101, 111, 112, 378/114, 115, 162, 165, 204, 210, 901; 250/370.01, 370.08, 370.09, 371; 382/128, 130, 131, 318, 319, 325
See application file for complete search history.

(56) References Cited

U.S. PATENT DOCUMENTS

| | | | | |
|---|---|---|---|---|
| 5,160,836 | A * | 11/1992 | Miyake ...................... | 250/208.1 |
| 5,600,143 | A * | 2/1997 | Roberts et al. ................ | 250/349 |
| 5,665,959 | A * | 9/1997 | Fossum et al. ............. | 250/208.1 |
| 2003/0048285 | A1* | 3/2003 | Okuzawa et al. ............ | 345/690 |
| 2005/0099515 | A1* | 5/2005 | Tsuruoka ...................... | 348/241 |
| 2006/0067579 | A1* | 3/2006 | Pirkl et al. .................... | 382/190 |
| 2010/0187430 | A1* | 7/2010 | Yoshimuta ............... | 250/370.09 |

FOREIGN PATENT DOCUMENTS

WO    WO 2011091896 A1 *  8/2011 ............. H04N 5/335

OTHER PUBLICATIONS

Willson, Paul D., Imaging Using Energy Discriminating Detector Array, American Institute of Physics, CP680 Application of Accelerators in Research and Industry: 17th International Conference, 2003, pp. 913-918.*

* cited by examiner

*Primary Examiner* — Anastasia Midkiff
(74) *Attorney, Agent, or Firm* — Oblon, McClelland, Maier & Neustadt, L.L.P.

(57) ABSTRACT

A Computed Tomography (CT) method, apparatus, and detector, which includes a plurality of energy-discriminating detector elements configured to capture incident X-ray photons emitted from an X-ray source. Each of the plurality of energy-discriminating detector elements of the detector is configured to have a respective bias voltage individually switched ON or OFF, based on a signal received from a controller.

14 Claims, 10 Drawing Sheets

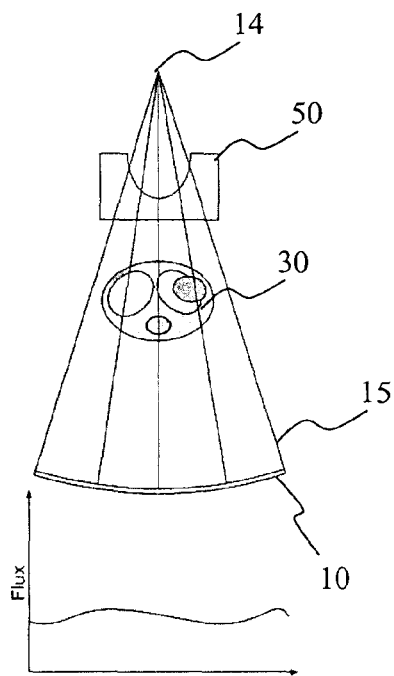 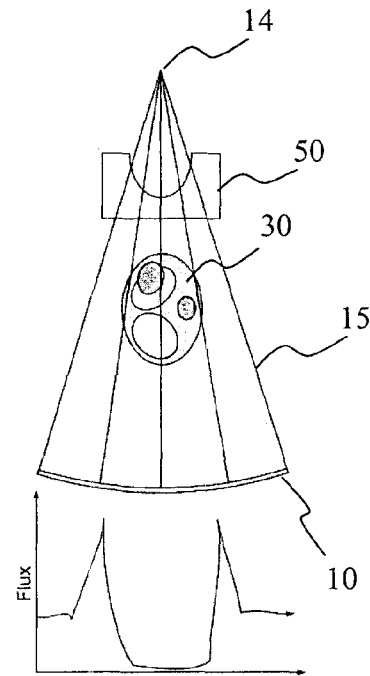
FIGURE 7  FIGURE 8
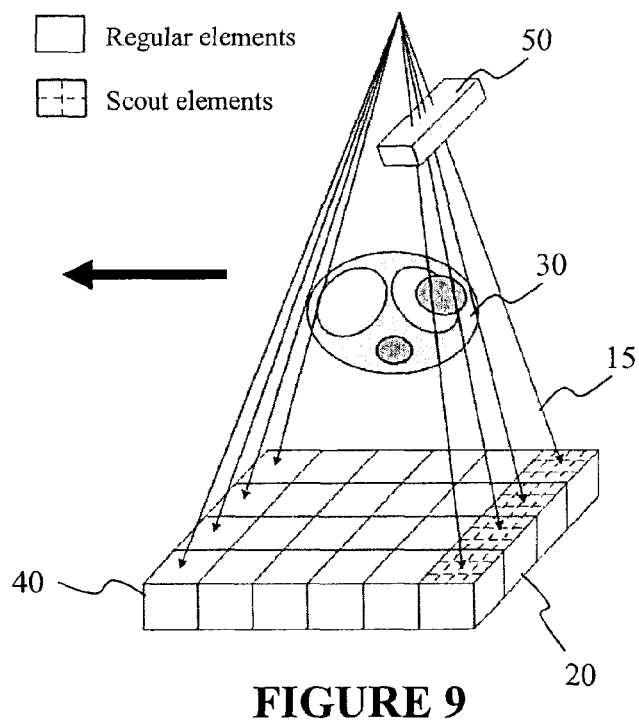
FIGURE 9

… (US 9,101,273 B2)

APPARATUS, DETECTOR, AND METHOD FOR APPLYING A PIXEL BY PIXEL BIAS ON DEMAND IN ENERGY DISCRIMINATING COMPUTED TOMOGRAPHY (CT) IMAGING

BACKGROUND

1. Field

The present disclosure generally relates to X-ray Computed Tomography (CT) imaging. In particular, embodiments herein relate to an apparatus, detector, and associated methods for switching ON or OFF a bias voltage of energy-discriminating detector elements based on contour estimation information.

2. Background

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed.

In one of many possible geometries, the X-ray source on top of the graph shown in FIG. 1 is emitting an X-ray beam forming a fan, traversing the object. While a wide range of values can exist, typically, the distance "C" is around 100 cm, "B" is around 60 cm, and "A" is around 40 cm. The principle of tomography requires that each point of the object is traversed by a collection of rays covering at least 180 degrees. Thus, the entire X-ray generator and detector assembly will rotate around an object. Mathematical considerations show that the tomographic conditions are met when a scan of 180 degrees plus the fan angle is performed.

Conventional X-ray detectors integrate the total electrical current produced in a radiation sensor, and disregard the amplitude information from individual photon detection events. Since the charge amplitude from each event is proportional to the photon's detected energy, this acquisition provides no information about the energy of individual photons, and is thus unable to capture the energy dependence of the attenuation coefficient in the object.

On the other hand, semiconductor X-ray detectors that are capable of single photon counting and individual pulse height analysis may be used. These X-ray detectors are made possible by the availability of fast semiconductor radiation sensors materials with room temperature operation and good energy resolution, combined with application-specific integrated circuits (ASICs) suitable for multi-pixel parallel readout and fast counting.

When operating such a photon-counting X-ray detector, a high bias voltage is applied across the sensor crystal such that the electron-hole pairs generated from the radiation interaction are rapidly swept toward the collecting electrodes. Each radiation interaction event results in a pulse sent to the readout electronics, which undergoes pulse height analysis and is counted.

One major advantage of such photon-counting detectors is that, when combined with pulse height analysis readout, spectral information can be obtained about the attenuation coefficient in the object. Conventional CT measures the attenuation at one average energy only, while in reality, the attenuation coefficient strongly depends on the photon energy. In contrast, with pulse height analysis, a system is able to categorize the incident X-ray photons into several energy bins based on their detected energy. This spectral information can effectively improve material discrimination and target contrast, all of which can be traded for a dose reduction to, for example, a patient.

One challenge with using such photon-counting detectors for medical CT applications is the very high X-ray flux required in most CT tasks. Unlike conventional X-ray detectors, single photon counting requires very fast sensor-crystal response and readout-electronics response. In a routine CT scan, as many as $10^8$ photons, or even more, can hit one detector element every second. At such high flux, the electron and hole carriers generated in the sensor do not have enough time to be fully collected at the electrodes and removed from the crystal bulk. For many semiconductors of interest for X-ray detection, this is especially pronounced for hole carriers, which travel more than ten times slower than the electrons. This, combined with crystal imperfections and defects that further trap the carriers, results in building up of charges from the uncollected carriers and an internal electric field.

This internal electric field ("$E_{int}$") is of opposite direction to the external electric field generated by the applied bias ("$T_{bias}$"). As a result, the net electric field inside the crystal is weakened, further preventing the full collection of the charge carriers. The net result will be the inability of the detector to respond to incoming radiation and count loss in the measured data. This phenomenon, referred to as "polarization," prevents semiconductor photon-counting detectors from fully realizing their potential in high-flux CT applications.

BRIEF DESCRIPTION OF THE DRAWINGS

The disclosure will be better understood from reading the description which follows and from examining the accompanying figures. These figures are provided solely as non-limiting examples of the embodiments. In the drawings:

FIGS. 7 and 8 illustrate examples of detector elements that may become heavily polarized by high flux;

FIG. 9 illustrates scout elements that dynamically follow the contour of an object during a helical scan;

DETAILED DESCRIPTION

Figure 1:
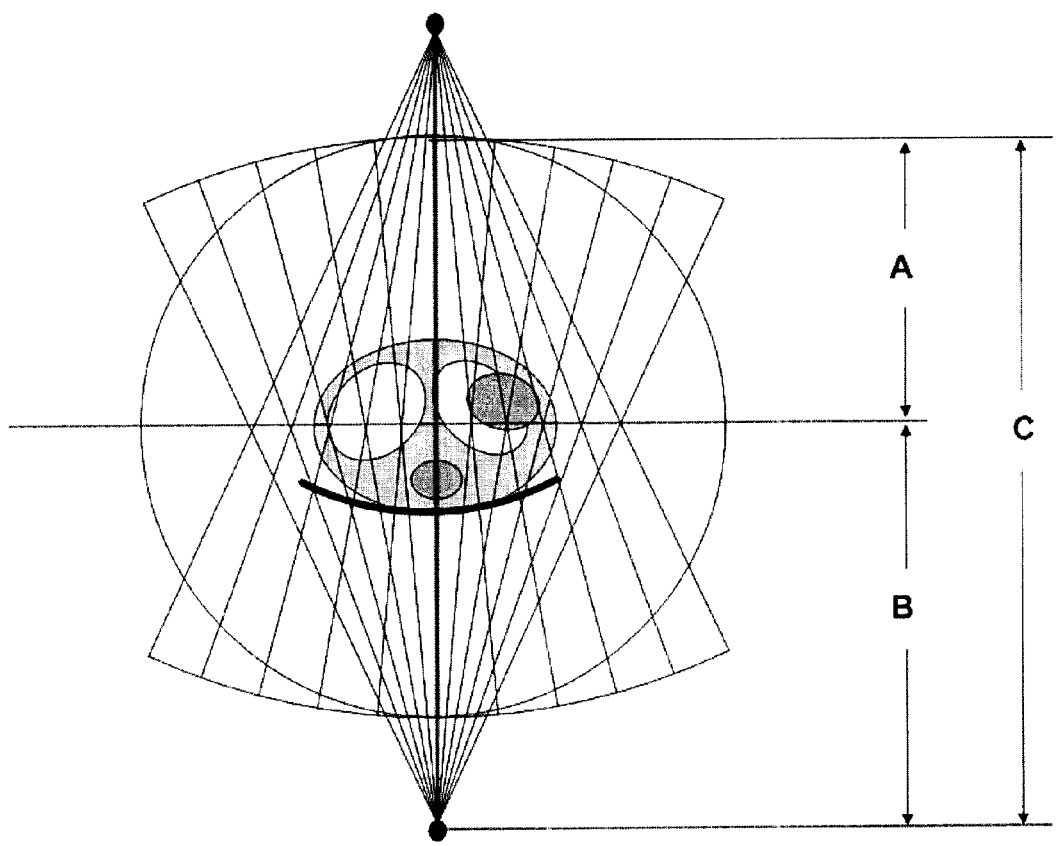
FIG. 1 illustrates an X-ray source emitting an X-ray beam forming a fan, traversing an object.

The present disclosure describes a CT apparatus, which includes a CT detector including a plurality of energy-discriminating detector elements configured to capture incident X-ray photons emitted from an X-ray source during a low-dose pre-scan of an object for a plurality of projection views, and a data acquisition unit configured to acquire data detected by the plurality of energy-discriminating detector elements during each of the plurality of projection views of the low-dose pre-scan. The CT apparatus further includes a contour calculation unit configured to calculate a contour of the object in each of the plurality of projection views, based on the acquired data, and a controller configured to individually switch a respective bias voltage of each of the plurality of energy-discriminating detector elements ON or OFF during a subsequent scan of the object, based on the calculated contour of the object.

The present disclosure also describes a method for a CT apparatus that includes a CT detector including a plurality of energy-discriminating detector elements configured to capture incident X-ray photons emitted from an X-ray source. The method of the present disclosure includes acquiring data detected by the plurality of energy-discriminating detector elements during each of a plurality of projection views of a low-dose pre-scan of an object, calculating a contour of the object in each of the plurality of projection views, based on the acquired data, and individually switching a respective bias voltage of each of the plurality of energy-discriminating detector elements ON or OFF during a subsequent scan of the object, based on the calculated contour of the object.

In addition, the present disclosure describes a CT detector, which includes a plurality of energy-discriminating detector elements configured to capture incident X-ray photons emitted from an X-ray source. In the CT detector of the present disclosure, each of the plurality of energy-discriminating detector elements is configured to have a respective bias voltage individually switched ON or OFF, based on a signal received from a controller.

Furthermore, the present disclosure describes a CT apparatus, which includes a CT detector. The CT detector includes a first plurality of energy-discriminating detector elements, the first plurality of energy-discriminating detector elements configured to capture incident X-ray photons during a scan of an object, and a second plurality of detector elements disposed at one end of the CT detector adjacent to the first plurality of energy-discriminating detector elements, the second plurality of detector elements configured to capture low-dose incident X-ray photons during the scan of the object, the second plurality of detector elements scanning a given portion of the object prior to the first plurality of energy-discriminating detector elements scanning the given portion of the object as the object moves over the CT detector. The CT apparatus of the present disclosure also includes a data acquisition unit configured to acquire data detected by the second plurality of detector elements during the scan, a contour calculation unit configured to calculate a contour of the object, based on the acquired data, and a controller configured to individually switch a respective bias voltage of each of the first plurality of energy-discriminating detector elements ON or OFF during the scan of the object, based on the calculated contour of the object.

Additionally, the second plurality of detector elements of the CT apparatus are energy-discriminating detector elements. Moreover, only the first plurality of energy-discriminating detector elements are energy-discriminating detector elements.

Further, the CT apparatus includes a pre-patient filter configured to provide the low-dose X-ray photons to the second plurality of detector elements during the scan of the object. In addition, only the second plurality of detector elements of the CT apparatus capture the low-dose incident X-ray photons, and only the first plurality of energy-discriminating detector elements of the CT apparatus capture non-low-dose incident X-ray photons.

The present disclosure also describes a method for a CT apparatus that includes a CT detector including a first plurality of energy-discriminating detector elements, the first plurality of energy-discriminating detector elements configured to capture incident X-ray photons during a scan of an object, and a second plurality of detector elements disposed at one end of the CT detector adjacent to the first plurality of energy-discriminating detector elements, the second plurality of detector elements configured to capture low-dose incident X-ray photons during the scan of the object, the second plurality of detector elements scanning a given portion of the object prior to the first plurality of energy-discriminating detector elements scanning the given portion of the object as the object moves over the CT detector. The method includes acquiring data detected by the second plurality of detector elements during the scan, calculating a contour of the object based on the acquired data, and individually switching a respective bias voltage of each of the first plurality of energy-discriminating detector elements ON or OFF during the scan of the object, based on the calculated contour of the object.

Next, the present disclosure describes a CT detector, which includes a first plurality of energy-discriminating detector elements, the first plurality of energy-discriminating detector elements configured to capture incident X-ray photons during a scan of an object, and a second plurality of detector elements disposed at one end of the CT detector adjacent to the first plurality of energy-discriminating detector elements, the second plurality of detector elements configured to capture low-dose incident X-ray photons during the scan of the object, the second plurality of detector elements scanning a given portion of the object prior to the first plurality of energy-discriminating detector elements scanning the given portion of the object as the object moves over the CT detector. Furthermore, in the CT detector, a respective bias voltage of each of the first plurality of energy-discriminating detector elements is individually switched ON or OFF during the scan of the object by a controller, based on a calculated contour of the object, the calculated contour being calculated based on data acquired by the second plurality of detector elements during the scan of the object.

In addition, the second plurality of detector elements of the CT detector are energy-discriminating detector elements. Moreover, only the first plurality of energy-discriminating detector elements of the CT detector are energy-discriminating detector elements.

Further, only the second plurality of detector elements of the CT detector capture the low-dose incident X-ray photons, and only the energy-discriminating plurality of detector elements of the CT detector capture non-low-dose incident X-ray photons.

Additionally, the present disclosure describes a CT detector, which includes a first plurality of energy-discriminating detector elements, and a second plurality of detector elements disposed at one end of the CT detector adjacent to the first plurality of energy-discriminating detector elements, the second plurality of detector elements scanning a given portion of an object prior to the first plurality of energy-discriminating detector elements scanning the given portion of the object as the object moves over the CT detector. In the CT detector of the present disclosure, each of the first plurality of energy-discriminating detector elements is configured to have a respective bias voltage individually switched ON or OFF, based on a signal received from a controller.

Generally, the present disclosure describes scanning techniques that can efficiently determine the view-by-view contour information of an object (e.g., a patient), as required by high-flux CT applications using bias-on-demand semiconductor photon-counting X-ray detectors.

Figure 2:
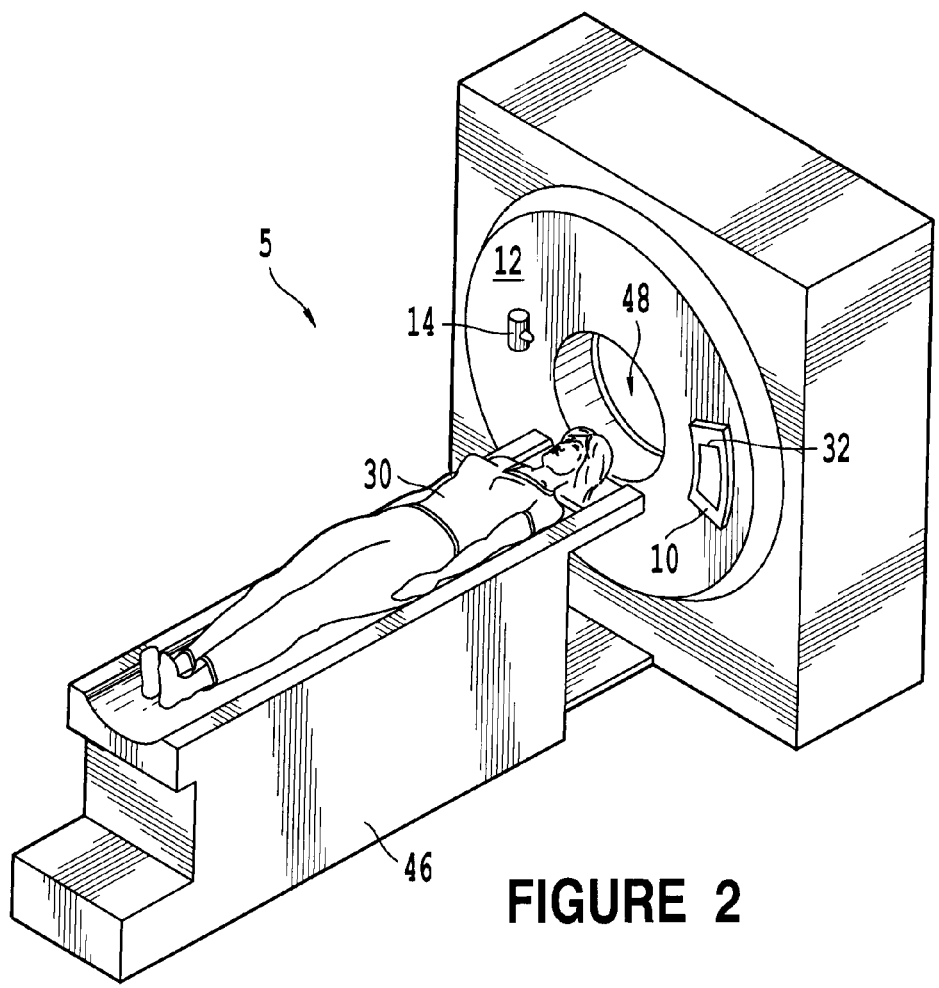
FIGS. 2 and 3 illustrate a Computed Tomography (CT) imaging system.
Figure 3:
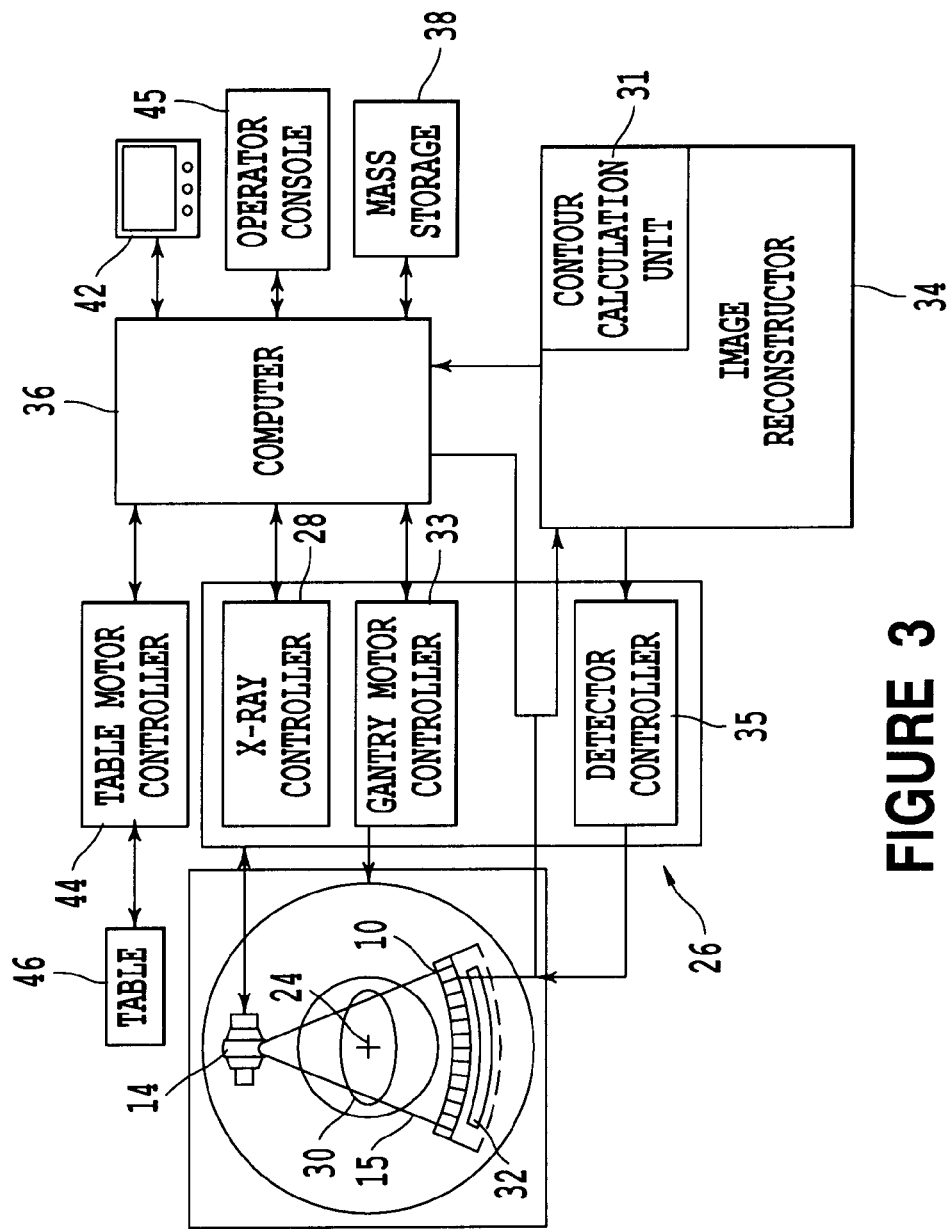

Referring to FIG. 2, a CT imaging apparatus/system 5 includes a gantry 12 representative of a CT scanner. Gantry 12 has an X-ray source 14 that projects a beam of X-rays 15 toward a detector 10 on the opposite side of the gantry 12, the detector 10 being formed by a plurality of elements, as shown in FIG. 3. The elements of the detector 10 sense the projected X-rays that pass through an object 30, and a data acquisition unit 32 converts the data to digital signals for subsequent processing. Each element of the detector 10 produces an analog electrical signal that represents the intensity of an impinging X-ray beam and hence the attenuated beam as it passes through the object 30. During a scan to acquire X-ray projection data, gantry 12 and the components mounted thereon rotate about a center of rotation 24.

The rotation of gantry 12 and the operation of X-ray source 14 are governed by a control mechanism 26 of the CT system 5. Control mechanism 26 includes an X-ray controller 28 that provides power and timing signals to the X-ray source 14, a gantry motor controller 33 that controls the rotational speed and position of gantry 12, and a detector controller 35 that controls the bias voltage of each of the elements of detector 10 in order to individually switch ON or OFF the bias voltage of each of the elements of detector 10. An image reconstructor 34 receives sampled and digitized X-ray data from data acquisition unit 32 and performs high speed reconstruction. The reconstructed image is applied as an input to a computer 36 which stores the image in a mass storage device 38. The image reconstructor 34 may also include a contour calculation unit 31 that calculates the contour of object 30 in a plurality of projection views. However, the contour calculation unit 31 may be separate from the image reconstructor 34.

Computer 36 also receives commands and scanning parameters from an operator via console 45 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to data acquisition unit 32, X-ray controller 28, and gantry motor controller 33. In addition, computer 36 operates a table motor controller 44 that controls a motorized table 46 to object 30 and gantry 12. Particularly, table 46 moves object 30 through a gantry opening 48 of FIG. 2 in whole or in part.

As discussed, the X-ray detector 10 detects and measures the incident X-ray intensity. Conventional X-ray detectors 10 integrate the total electrical current produced in the radiation sensor, and disregard the amplitude information from individual photon detection events. Since the charge amplitude from each event is proportional to the photon's detected energy, this acquisition provides no information about the energy of individual photons, and is thus unable to capture the energy dependence of the attenuation coefficient in the object 30.

Figure 4:
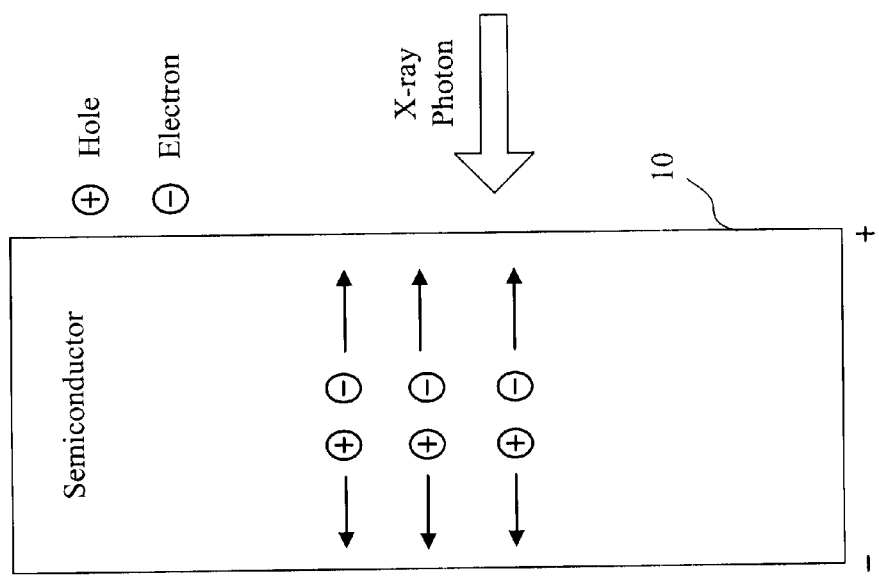

On the other hand, semiconductor X-ray detectors 10 that are capable of single photon counting and individual pulse height analysis may be used. These X-ray detectors 10 are made possible by the availability of fast semiconductor radiation sensors materials with room temperature operation and good energy resolution, combined with application-specific integrated circuits (ASICs) suitable for multi-pixel parallel readout and fast counting. See FIG. 4.

Figure 5:
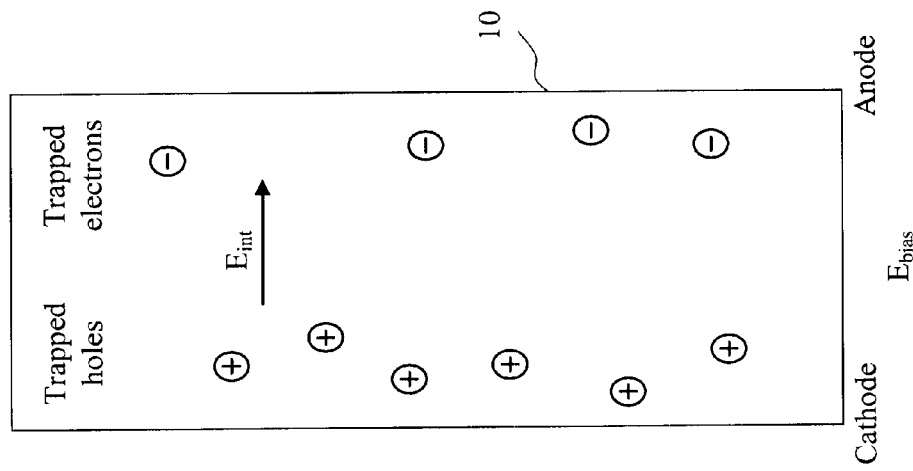
FIGS. 4 and 5 illustrate semiconductor X-ray detectors.

When operating such a photon-counting X-ray detector 10, a high bias voltage is applied across the sensor crystal such that the electron-hole pairs generated from the radiation interaction are rapidly swept toward the collecting electrodes, anode, and a cathode, respectively. Note that the anode can be either on the front or back side of the crystal, depending on the specific application of interest and thickness of the crystal (in FIG. 5, the anode is on the front side). Each pulse radiation interaction event results In a pulse sent to the readout electronics, which undergoes pulse height analysis and is counted.

One major advantage of such photon-counting detectors is that, when combined with pulse height analysis readout, spectral information can be obtained about the attenuation coefficient in the object. Note that a photon-counting detector can also be referred to as an energy-discriminating detector (if pulse height analysis is performed). Conventional CT measures the attenuation at one average energy only, while in reality, the attenuation coefficient strongly depends on the photon energy. In contrast, with pulse height analysis, a system is able to categorize the incident X-ray photons into several energy bins based on their detected energy. This spectral information can effectively improve material discrimination and target contrast, all of which can be traded for a dose reduction to the patient.

One challenge with using such photon-counting detectors for medical CT applications is the very high X-ray flux required in most CT tasks. Unlike conventional X-ray detectors, single photon counting requires very fast sensor-crystal response and readout-electronics response. In a routine CT scan, as many as $10^8$ photons, or even more, can hit one detector element every second. At such high flux, the electron and hole carriers generated in the sensor do not have enough time to be fully collected at the electrodes and removed from the crystal bulk. For many semiconductors of interest for X-ray detection, this is especially pronounced for hole carriers, which travel more than ten times slower than the electrons. This, combined with crystal imperfections and defects that further trap the carriers, results in building up of charges from the uncollected carriers and an internal electric field.

This internal electric field ("$E_{int}$") is of opposite direction to the external electric field generated by the applied bias ("$E_{bias}$"). See FIG. 5. As a result, the net electric field inside the crystal is weakened, further preventing the full collection of the charge carriers. The net result will be the inability of the detector 10 to respond to incoming radiation and count loss in the measured data. This phenomenon, referred to as "polarization," prevents semiconductor photon-counting detectors 10 from fully realizing their potential in high-flux CT applications.

Figure 6:
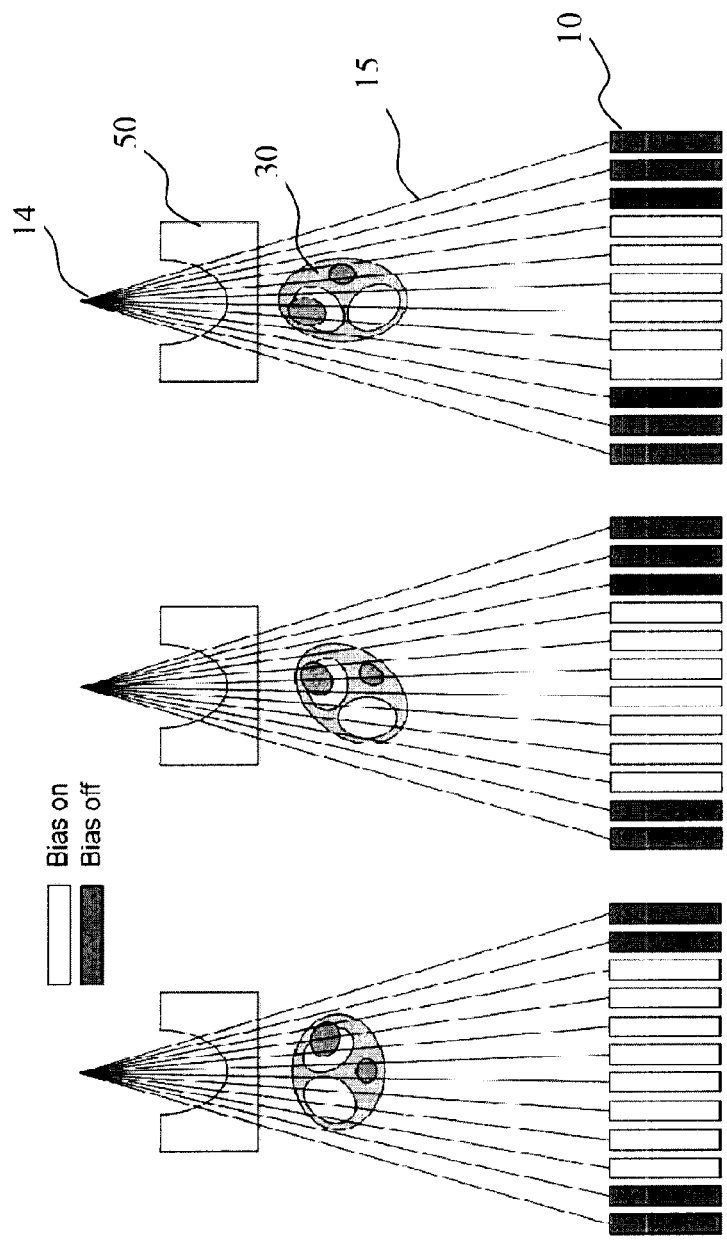
FIG. 6 illustrates examples of bias voltage of detector elements being turned ON and OFF.

In order to minimize the degradation effect of polarization when operating photon-counting semiconductor detectors 10 under a high-flux X-ray irradiation, a "bias-on-demand" design may be used. In this embodiment, the bias voltage on a detector element is automatically switched off when the system detects that the element is under direct, unobstructed, X-ray exposure at that particular view (i.e., no object 30 in the path between the X-ray source 14 and the element). See FIG. 6. This prevents the detector element from polarizing under a high-flux irradiation, ensuring that it will function properly when the object 30 later moves into its view. Details on controlling the bias voltage of each detector element is described in more detail below.

In a CT scan, a scanogram or scout view is first performed on a patient 30 with the X-ray tube 14 and the detector 10 staying stationary and the patient table 46 traveling at a constant speed. In addition to determining the patient's anatomical landmarks, the scanogram aims to determine the exact location and range of the patient 30. Although this information is useful for selecting the optimal scan parameters (collimator aperture, bowtie filter, tube voltage and current, reconstruction field-of-view, etc.) and minimizing unnecessary radiation exposure to the patient 30, it is not sufficient to produce the view-by-view contour information required by the bias-on-demand design, since only one-view radiographic images are obtained.

A scanogram has lower spatial resolution than a normal scan. Some form of edge enhancement filtering or dynamic range compression is often applied prior to display. Scanograms are used primarily to localize body structures for subsequent CT scans, and to display the locations of acquired CT slices.

As a scanogram is similar to conventional radiography, the projection image is only acquired at one (or a few) fixed view(s) of the object (e.g., Anterior-Posterior (A-P) position for most clinical routines). The human body, on the other hand, has elliptical cross sections, and therefore, different widths in different projection views. An A-P position projection measures the long axis of the ellipse. If this width is used for all views, detector elements that are assumed to be behind the object can, in other views, find themselves under direct X-ray exposure with the bias incorrectly ON. These elements are highly likely to become heavily polarized by the high flux and inoperable for the upcoming views. See FIGS. 7 and 8.

In an embodiment of the present disclosure, instead of a scanogram, an ultra-low-dose tomographic pre-scan is performed to estimate the entire contour of a patient 30. The pre-scan is performed in a plurality of projection views, and a contour of the patient 30 is estimated for each of the projection views. The contour estimation information is subsequently used (by a detector controller 35 of the system, for example) to turn the bias voltage of each of the detector elements ON or OFF during a regular, full scan of the object 30. In other words, the contour estimation information is used to switch the bias voltage of the detector elements outside the object 30 projection OFF in order to prevent polarization. See FIG. 6.

Since only the outline of the object 30 is needed for the aforementioned pre-scan, there is little concern for image quality. Thus, the pre-scan uses lower techniques (mAs) and thicker pre-patient filters than a regular scan in order to minimize the added dose to the patient. Inter-view interpolation can be performed for data to be used in the full scan, which may use more projection views. This technique can be applied to circular, helical, or planar scans. Furthermore, the detector elements used with this technique can be photon-counting detectors (i.e., energy-discriminating detectors).

As shown in FIG. 9, a second embodiment of the present disclosure dedicates a front segment or region of detector elements (i.e., "scout elements" 20) to dynamically follow the contour of the object 30 during a helical scan. Note that in FIG. 9, the arrow indicates that the object 30 is moving from right to left. Thus, as the object 30 moves to the left, the scout elements 20 are first used in performing the pre-scan, and then, as the object 30 continues moving left, the regular elements 40 are used in performing a regular scan of the object 30. Although scout elements 20 are shown as a row in FIG. 9, it is to be understood that the scout elements 20 may include a plurality of rows. Scout elements 20 may also encompass a particular, predefined region of detector 10.

Similar to the above-identified technique, since no interior details and image quality are required, a pre-patient filter 50 (in addition to the standard bowtie and flat filters) is placed to attenuate the rays 15 transmitted toward the scout elements 20.

Also note that the scout detector elements 20 and the regular detector elements 40 can be different. For example, the scout detector elements 20 can be either photon-counting detectors (i.e., energy-discriminating detectors), the same as the regular elements 40, or conventional X-ray detectors elements, which are relatively easier and cheaper to manufacture.

In the present embodiment, the scout elements 20 are used to perform the pre-scan for a plurality of projection views, and a contour of the patient is estimated for each of the projection views. The contour estimation information is subsequently used (e.g., by detector controller 35) to turn the bias voltage of each of the regular detector elements 40 ON or OFF during the subsequent regular, full scan of the object 30. In other words, the contour estimation information is used to switch the bias voltage of the regular detector elements 40 that are outside the object 30 projection OFF in order to prevent polarization. See FIG. 6.

Note that the pre-patient filter 50 is used to attenuate the rays 15 toward the scout elements 20 during the pre-scan. However, the pre-patient filter 50 is not used during the subsequent regular, full scan of the object 30. In other words, the pre-patient filter 50 is used only with respect to the scout elements 20 during the pre-scan, and is not used with respect to the regular detector elements 40 in the full scan of object 30.

Note that the number of projection views used during the pre-scan can be predetermined or predefined in advance of the pre-scan. The number of projection views can depend on factors such as the desired resolution.

Figure 10:
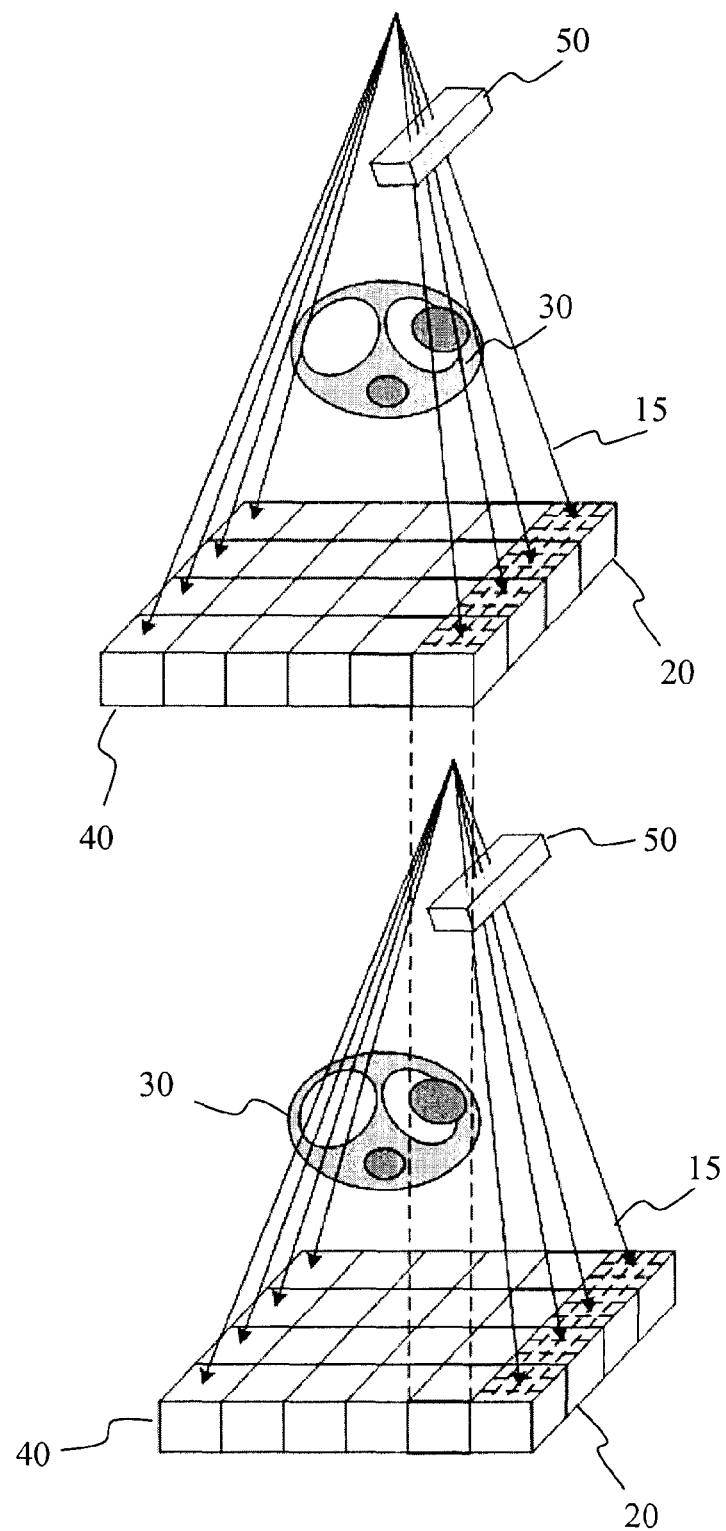
FIG. 10 illustrates an example of a scan according to an embodiment of the present disclosure.

As illustrated in the example of FIG. 10, if the helical pitch is selected such that after one rotation, the first segment of regular detector elements 40 is in the position with respect to the object of the scout elements 20 one rotation ago, the scout elements 20 provide an approximation of the contour information for the first segment of regular elements 10. This is an approximation since their position with respect to the source differs by one segment thickness (i.e., width).

Due to the fixed segment thickness and helical pitch, it may not be possible for all the regular detector segments 40 to have a "matching" scout measurement, as described above. In this situation, interpolation between the two closest sets of measurements is performed to approximate the contour and width of the object at the current detector segment and projection view.

A consequence of this embodiment is that different parts of the same detector 10 will be exposed to a low flux, while at the same time, other parts will be operated at normal, diagnostic quality fluxes.

Figure 11:
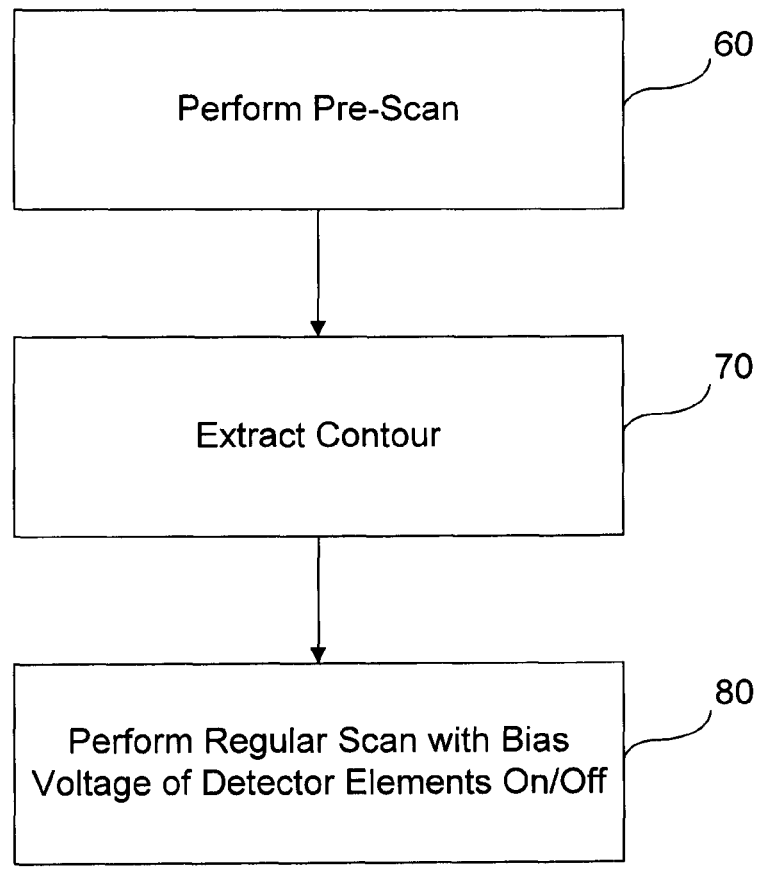
FIG. 11 illustrates a flowchart of a method of the present disclosure.

FIG. 11 is a flowchart of a method according to one embodiment. In step 60, a pre-scan of object 30 is performed for a plurality of projection views. This pre-scan may be performed using all of the detector elements or, for an embodiment employing scout elements 20, by the scout elements 20, as discussed above with respect to FIG. 9.

Next, in step 70, the contour of object 30 is extracted or calculated for each of the projection views based on the data generated during the pre-scan. This calculation is performed by a contour calculation unit 31, which can be included in the image reconstructor 34, as shown in FIG. 3.

In step 80, a regular scan is performed of object 30. This regular scan is performed with the bias voltage of the detector elements dynamically turned ON or OFF depending on the information of the contour acquired in step 70. In other words, the contour information is used to dynamically switch the bias voltage of the detector elements that are outside the object 30 projection OFF in order to prevent polarization. See FIG. 6.

Figure 12:
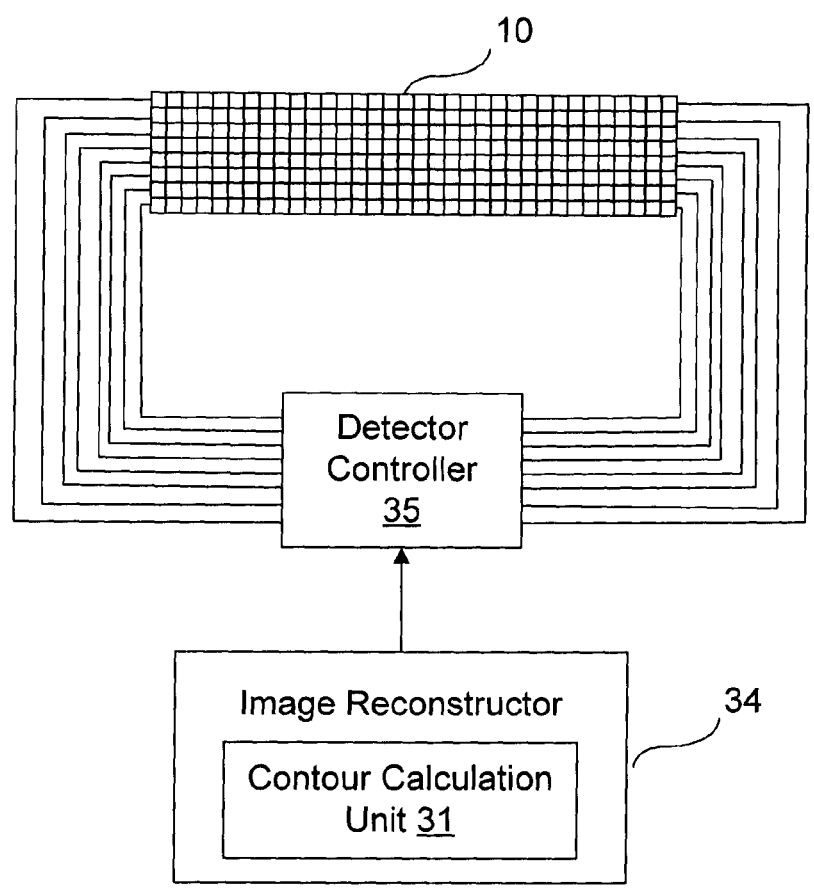
FIG. 12 illustrates a controller that controls the bias voltage of each detector element.

FIG. 12 shows a detector controller 35, which is electrically connected to each of the elements of detector 10. As discussed above, detector controller 35 controls the bias voltage of each of the elements of the detector 10 by individually switching the bias voltage of each of the elements of the detector 10 ON or OFF based on the information calculated in step 70 by the contour calculation unit 31, which is located in the image reconstructor 34.

In one embodiment, the pre-patient filter, which is used to decrease the radiation flux to the scouting detector elements, can be alternatively implemented by placing an attenuator directly on the detector surface. However, the pre-patient filter solution described above is preferable, as it would decrease the radiation dose to the patient.

The embodiments of the present disclosure provide certain advantages. The first embodiment provides, for example, view-by-view contour information of the object that is required to enable the bias-on-demand photon-counting X-ray detectors. In addition, the second embodiment can, for example, dynamically obtain the required information during an active scan. Additionally, with properly selected filters and scanning techniques, the added dose to the patient is minimal.

Thus, in summary, embodiments of the present disclosure can effectively measure the width and range of the object 30 (e.g., human head, chest, abdomen, or the like) at any projection view during the scan, in order to determine which detector elements should have their bias voltage switched off (those outside the object 30 projection) to prevent polarization.

The embodiments of the present disclosure monitor the view-by-view contour information of the object to control "bias-on-demand" semiconductor photon-counting X-ray detectors 10 so as to more effectively reduce semiconductor polarization when used under high-flux conditions.

Figure 13:
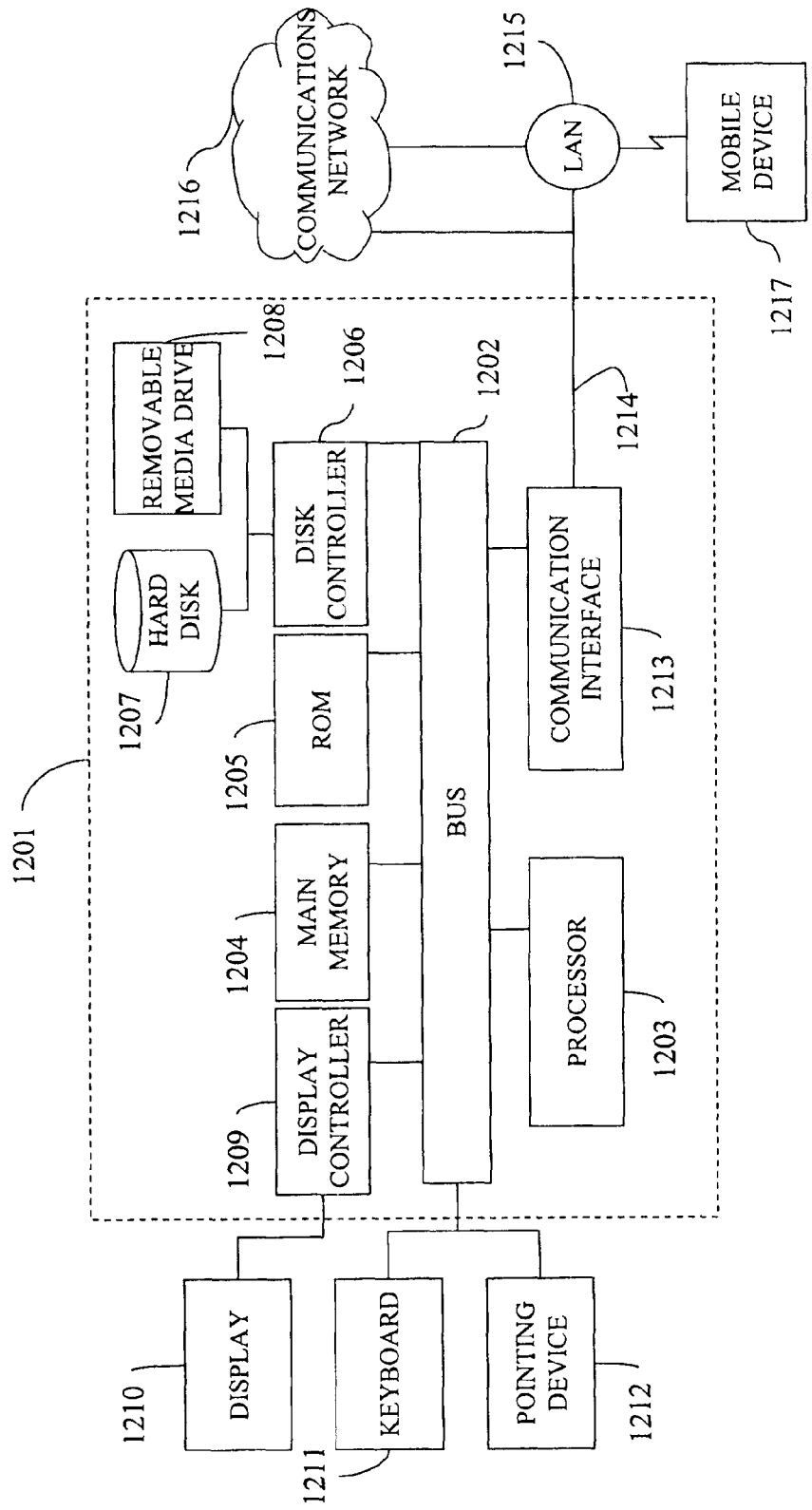
FIG. 13 illustrates a computer system upon which an embodiment of the present disclosure may be implemented.

Various components of the CT system 5 described above can be implemented using a computer system or programmable logic. FIG. 13 illustrates a computer system 1201 upon which embodiments of the present disclosure may be implemented. The computer system 1201 may include, for example, computer 36 and the different processing units (i.e., a data acquisition unit 32, an image reconstructor 34, and a contour calculation unit 31) of the CT apparatus and/or system, which perform the above-described process.

The computer system 1201 includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as display 42 or a liquid crystal display (LCD), for displaying information to a computer user. The computer system includes input devices, such as a keyboard 1211 and a pointing device 1212, for interacting with a computer user and providing information to the processor 1203. The pointing device 1212, for example, may be a mouse, a trackball, a finger for a touch screen sensor, or a pointing stick for communicating direction information and command selections to the processor 1203 and for controlling cursor movement on the display 1210.

The computer system 1201 performs a portion or all of the processing steps of the present disclosure in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1201, for driving a device or devices for implementing the invention, and for enabling the computer system 1201 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1203 for execution. A computer readable medium may take many forms, including but not limited to, non-volatile media or volatile media. Non-volatile media includes, for example, optical, magnetic disks, and magneto-optical disks, such as the hard disk 1207 or the removable media drive 1208. Volatile media includes dynamic memory, such as the main memory 1204. Transmission media, on the contrary, includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1201 may receive the data on the telephone line and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an integrated services digital network (ISDN) card. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc.). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214 and the communication interface 1213. Moreover, the network link 1214 may provide a connection through a LAN 1215 to a mobile device 1217 such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, comprising:
   a CT detector including a plurality of energy-discriminating detector elements configured to capture incident X-ray photons emitted from an X-ray source during a low-dose pre-scan of an object for a plurality of projection views;
   a data acquisition unit configured to acquire data detected by the plurality of energy-discriminating detector elements during each of the plurality of projection views of the low-dose pre-scan;
   a contour calculation unit configured to calculate a contour of the object in each of the plurality of projection views, based on the acquired data; and
   a controller configured to individually switch a respective bias voltage of each of the plurality of energy-discriminating detector elements ON or OFF during a subsequent scan of the object, based on the calculated contour of the object.

2. A method for a computed-tomography (CT) apparatus that includes a CT detector including a plurality of energy-discriminating detector elements configured to capture incident X-ray photons emitted from an X-ray source, the method comprising:
   acquiring data detected by the plurality of energy-discriminating detector elements during each of a plurality of projection views of a low-dose pre-scan of an object;
   calculating a contour of the object in each of the plurality of projection views, based on the acquired data; and
   individually switching a respective bias voltage of each of the plurality of energy-discriminating detector elements ON or OFF during a subsequent scan of the object, based on the calculated contour of the object.

3. A computed-tomography (CT) detector, comprising:
   a plurality of energy-discriminating detector elements configured to capture incident X-ray photons emitted from an X-ray source,
   wherein each of the plurality of energy-discriminating detector elements is configured to have a respective bias voltage individually switched ON or OFF, based on a signal received from a controller for each of a plurality of projection views.

4. A computed-tomography (CT) apparatus, comprising:
   a CT detector including
      a first plurality of energy-discriminating detector elements, the first plurality of energy-discriminating detector elements configured to capture incident X-ray photons during a scan of an object; and
      a second plurality of detector elements disposed at one end of the CT detector adjacent to the first plurality of energy-discriminating detector elements, the second plurality of detector elements configured to capture low-dose incident X-ray photons during the scan of the object, the second plurality of detector elements scanning a given portion of the object prior to the first plurality of energy-discriminating detector elements scanning the given portion of the object as the object moves over the CT detector;
   a data acquisition unit configured to acquire data detected by the second plurality of detector elements during the scan;
   a contour calculation unit configured to calculate a contour of the object, based on the acquired data; and
   a controller configured to individually switch a respective bias voltage of each of the first plurality of energy-discriminating detector elements ON or OFF during the scan of the object, based on the calculated contour of the object.

5. The CT apparatus of claim 4, wherein the second plurality of detector elements are energy-discriminating detector elements.

6. The CT apparatus of claim 4, wherein only the first plurality of energy-discriminating detector elements are energy-discriminating detector elements.

7. The CT apparatus of claim 4, further comprising:
a pre-patient filter configured to provide the low-dose X-ray photons to the second plurality of detector elements during the scan of the object.

8. The CT apparatus of claim 4, wherein
only the second plurality of detector elements capture the low-dose incident X-ray photons, and
only the first plurality of energy-discriminating detector elements capture non-low-dose incident X-ray photons.

9. A method for a computed-tomography (CT) apparatus that includes a CT detector including a first plurality of energy-discriminating detector elements, the first plurality of energy-discriminating detector elements configured to capture incident X-ray photons during a scan of an object, and a second plurality of detector elements disposed at one end of the CT detector adjacent to the first plurality of energy-discriminating detector elements, the second plurality of detector elements configured to capture low-dose incident X-ray photons during the scan of the object, the second plurality of detector elements scanning a given portion of the object prior to the first plurality of energy-discriminating detector elements scanning the given portion of the object as the object moves over the CT detector, the method comprising:
acquiring data detected by the second plurality of detector elements during the scan;
calculating a contour of the object based on the acquired data; and
individually switching a respective bias voltage of each of the first plurality of energy-discriminating detector elements ON or OFF during the scan of the object, based on the calculated contour of the object.

10. A computed-tomography (CT) detector, comprising:
a first plurality of energy-discriminating detector elements, the first plurality of energy-discriminating detector elements configured to capture incident X-ray photons during a scan of an object; and
a second plurality of detector elements disposed at one end of the CT detector adjacent to the first plurality of energy-discriminating detector elements, the second plurality of detector elements configured to capture low-dose incident X-ray photons during the scan of the object, the second plurality of detector elements scanning a given portion of the object prior to the first plurality of energy-discriminating detector elements scanning the given portion of the object as the object moves over the CT detector,
wherein a respective bias voltage of each of the first plurality of energy-discriminating detector elements is individually switched ON or OFF during the scan of the object by a controller, based on a calculated contour of the object, the calculated contour being calculated based on data acquired by the second plurality of detector elements during the scan of the object.

11. The CT detector of claim 10, wherein the second plurality of detector elements are energy-discriminating detector elements.

12. The CT detector of claim 10, wherein only the first plurality of energy-discriminating detector elements are energy-discriminating detector elements.

13. The CT detector of claim 10, wherein
only the second plurality of detector elements capture the low-dose incident X-ray photons, and
only the energy-discriminating plurality of detector elements capture non-low-dose incident X-ray photons.

14. A computed-tomography (CT) detector, comprising:
a first plurality of energy-discriminating detector elements; and
a second plurality of detector elements disposed at one end of the CT detector adjacent to the first plurality of energy-discriminating detector elements, the second plurality of detector elements scanning a given portion of an object prior to the first plurality of energy-discriminating detector elements scanning the given portion of the object as the object moves over the CT detector,
wherein each of the first plurality of energy-discriminating detector elements is configured to have a respective bias voltage individually switched ON or OFF, based on a signal received from a controller for each of a plurality of projection views.

* * * * *